United States Patent
Ng et al.

(10) Patent No.: US 7,645,911 B2
(45) Date of Patent: Jan. 12, 2010

(54) PROCESS FOR PREPARATION OF PARICALCITOL AND INTERMEDIATES THEREOF

(75) Inventors: Chze Siong Ng, Taoyuan (TW); Ching-Peng Wei, Taoyuan (TW)

(73) Assignee: Formosa Laboratories, Inc., Taoyuan (TW)

( * ) Notice: Subject to any disclaimer, the term of this patent is extended or adjusted under 35 U.S.C. 154(b) by 0 days.

(21) Appl. No.: 12/179,902

(22) Filed: Jul. 25, 2008

(65) Prior Publication Data

US 2009/0149678 A1    Jun. 11, 2009

Related U.S. Application Data

(62) Division of application No. 11/953,527, filed on Dec. 10, 2007, now Pat. No. 7,491,712.

(51) Int. Cl.
*C07C 35/22* (2006.01)
(52) U.S. Cl. ...................................... 568/819
(58) Field of Classification Search ................ 514/167, 514/653; 552/653
See application file for complete search history.

(56) References Cited

U.S. PATENT DOCUMENTS

| 4,195,027 A | 3/1980 | DeLuca et al. |
| 5,086,191 A | 2/1992 | DeLuca et al. |
| 5,237,110 A * | 8/1993 | DeLuca et al. ............. 568/665 |
| 5,587,497 A | 12/1996 | DeLuca et al. |
| 5,710,294 A | 1/1998 | DeLuca et al. |
| 5,880,113 A | 3/1999 | DeLuca et al. |
| 6,359,012 B1 * | 3/2002 | Meckler et al. ............. 514/653 |

FOREIGN PATENT DOCUMENTS

| EP | 0387077 | 9/1990 |
| EP | 0480572 | 4/1992 |
| WO | 9103246 | 3/1991 |

OTHER PUBLICATIONS

Herbert E. Paaren et al.,; Electrophilic Addition of OsO4 to 25-Hydroxycholecaliferol and Its 3,5-Cyclo Derivative; Journal;1983; pp. 3819-3821; vol. 48, No. 21; Journal of Organic Chemistry; American Chemical Society.
Lisa D. Coutts et al.,; A Stereospecific Synthesis of 24(S)-Hydroxyvitamin D2 . . . ; Journal; 2002; pp. 246-255; vol. 6, No. 3; Organic Process Research & Development; American Chemical Society.

* cited by examiner

*Primary Examiner*—Daniel M Sullivan
*Assistant Examiner*—Chukwuma O Nwaonicha
(74) *Attorney, Agent, or Firm*—WPAT, P.C.; Anthony King (57) ABSTRACT

The invention relates to a novel process for the preparation of Paricalcitol and intermediates thereof.

14 Claims, 2 Drawing Sheets

PROCESS FOR PREPARATION OF PARICALCITOL AND INTERMEDIATES THEREOF

CROSS-REFERENCE TO RELATED APPLICATIONS

This application claims priority to, and is a Divisional of, U.S. patent Ser. No. 11/953,527, filed on Dec. 10, 2007, now pending which is hereby incorporated by reference in its entirety. Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

FIELD OF THE INVENTION

This invention relates to biologically active 19-nor-analogs of 1α-hydroxylated vitamin D compounds. More specifically, the invention relates to a novel process for the preparation of Paricalcitol and intermediates thereof.

BACKGROUND OF THE INVENTION

The hormone, 1α-hydroxylated metabolites of vitamin D—most importantly 1α,25-dihydroxyvitamin D3 and 1α,25-dihydroxyvitamin D2—are known as highly potent regulators of calcium homeostasis in animals and humans, and more recently their activity in cellular differentiation has also been established. As a consequence, many structural analogs of these metabolites, such as compounds with different side chain structures, different hydroxylation patterns, or different stereochemistry, have been prepared and tested. Important examples of such analogs are 1α-hydroxyvitamin D3, 1α-hydroxyvitamin D2, various side chain fluorinated derivatives of 1α,25-dihydroxyvitamin D3, and side chain homologated analogs. Several of these known compounds have been found to exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, and certain malignancies.

Paricalcitol is a vitamin $D_2$ derived sterol lacking the carbon-19 methylene group found in all natural vitamin D metabolites. A class of vitamin D-related compounds, namely the 1α-hydroxy-19-nor-vitamin D analogs, as well as a general method for their chemical synthesis, are disclosed in U.S. Pat. No. 4,195,027, EP 0,387,077, U.S. Pat. No. 5,086,191, U.S. Pat. No. 5,237,110, U.S. Pat. No. 5,342,975, U.S. Pat. No. 5,880,113, U.S. Pat. No. 5,587,497, and U.S. Pat. No. 5,710,294. The compounds exhibit pronounced activity in calcium regulation and in arresting the proliferation of undifferentiated cells, including malignant cells, and in inducing their differentiation, and thus represent novel therapeutic agents for the treatment of malignant and other diseases characterized by the proliferative growth of undifferentiated cells. WO 9,103,246 discloses the use of the vitamin D-related compounds to treat the acquired immune deficiency syndrome (AIDS), and its related and derived analogs. EP 0,480,572 discloses compositions containing vitamin D compounds for cosmetic uses. The 19-nor-vitamin D compounds have the formula:

wherein $X^1$ and $X^2$ are each selected from hydrogen, acyl, alkylsilyl and alkoxyalkyl, and where R is selected from alkyl, hydrogen, hydroxyalkyl, said hydroxyalkyl having from 2 to 5 carbon atoms, fluoroalkyl and a side chain of the formula:

wherein $R^1$ represents hydrogen, hydroxy or O-acyl, $R^2$ and $R^3$ are each selected from alkyl, hydroxyalkyl and fluoroalkyl, or, when taken together represent the group —(CH2)m—where m is an integer having a value of from 2 to 5, $R^4$ is selected from hydrogen, hydroxy, fluorine, O-acyl, alkyl, hydroxyalkyl and fluoroalkyl, $R^5$ is selected from hydrogen, fluorine, alkyl, hydroxyalkyl and fluoroalkyl, or $R^4$ and $R^5$ taken together represent double-bonded oxygen, $R^6$ and $R^7$ are each selected from hydrogen, hydroxy, O-acyl, fluorine and alkyl, or, $R^6$ and $R^7$ taken together form a carbon-carbon double bond, and wherein n is an integer having a value of from 1 to 5 and wherein any of the groups —CH(CH3)-, —CH($R^7$)—, or —CH($R^6$)— at positions 20, 22 and 23, respectively, may be replaced by an oxygen atom, with the proviso that when n is 2 to 5 each $R^4$ is independently selected from hydrogen, hydroxy, fluorine, O-acyl, alkyl, hydroxyalkyl and fluoroalkyl, and each $R^5$ is independently selected from hydrogen, fluorine, alkyl, hydroxyalkyl and fluoroalkyl.

Two areas that have been pursued in an effort to identify novel vitamin D compounds with lowered calcemic activity are (1) placement of the hydroxyl group in the side chain on C-24 rather than C-25 and (2) the use of prodrugs (such as Coutts. et al., "A stereospecific synthesis of 24(s)-hydroxyvitamin D2, a prodrug for 1α, 24(S)-dihydroxyvitamin D2", Organic Process Research & Development. 2002, 6, 246~255 or U.S. Pat. No. 6,359,012) discloses the first stereospecific synthesis of 24(S)-hydroxyvitamin D2.

SUMMARY OF THE INVENTION

The present invention provides a compound having formula I

I wherein $R_1$ is $C_{1-6}$ alkoxy;

$R_2$ is hydrogen, OH or methyl-OH;

$R_3$ is hydrogen, OH or methyl-OH;

$R_2$ and $R_3$ together form a double bond or oxo (=O);

$R_4$ is hydrogen, OH, O-acyl, O—$C_{1-6}$ alkylsilyl or $C_{1-6}$ alkyloxy-$C_{1-6}$ alkyl;

$R_5$ is $C_{1-6}$ alkyl, $C_{1-6}$ alkyloxy-$C_{1-6}$ alkyl or aryl; and $R_6$ is $C_{1-6}$ alkyl, $C_{1-6}$ alkyloxy-$C_{1-6}$ alkyl or aryl.

The present invention also provides a compound having formula II

II

Where in $X_1$ is hydrogen, acyl, $C_{1-6}$ alkylsilyl or $C_{1-6}$ alkyloxy-$C_{1-6}$ alkyl;

$X_2$ is hydrogen, acyl, $C_{1-6}$ alkylsilyl or $C_{1-6}$ alkyloxy-$C_{1-6}$ alkyl;

$R_5$ is $C_{1-6}$ alkyl, $C_{1-6}$ alkyloxy-$C_{1-6}$ alkyl or aryl; and $R_6$ is $C_{1-6}$ alkyl, $C_{1-6}$ alkyloxy-$C_{1-6}$ alkyl or aryl.

The present invention further provides a process for preparing a compound having a formula wherein $X_2$ is hydrogen, acyl, $C_{1-6}$ alkylsilyl or $C_{1-6}$ alkyloxy-$C_{1-6}$ alkyl; and $R_4$ is hydrogen, OH, O-acyl, O—$C_{1-6}$ alkylsilyl or $C_{1-6}$ alkyloxy-$C_{1-6}$ alkyl; said process comprising reacting an intermediate compound of formula 16

16 with n-butyl lithium and a compound having a following formula wherein $R_7$ is $C_{1-6}$ alkylsilyloxy, in dry THF.

DETAILED DESCRIPTION OF THE INVENTION

Figure 1:
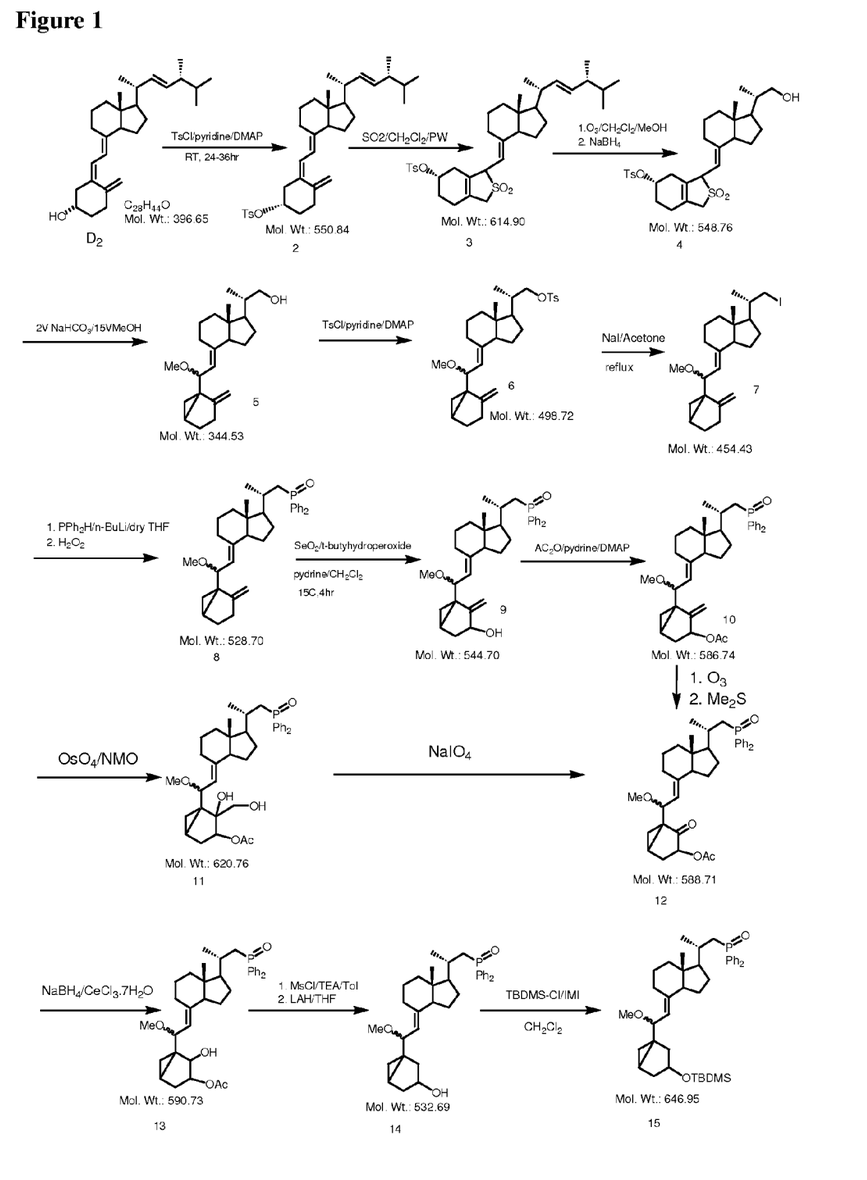
FIG. 1 illustrates the preparation of the compounds of the present invention.

The present invention relates to a compound having formula I wherein

R$_1$ is C$_{1-6}$ alkoxy;

R$_2$ is hydrogen, OH or methyl-OH;

R$_3$ is hydrogen, OH or methyl-OH;

R$_2$ and R$_3$ together form a double bond or oxo (=O);

R$_4$ is hydrogen, OH, O-acyl, O—C$_{1-6}$ alkylsilyl or C$_{1-6}$ alkyloxy-C$_{1-6}$ alkyl;

R$_5$ is C$_{1-6}$ alkyl, C$_{1-6}$ alkyloxy-C$_{1-6}$ alkyl or aryl; and

R$_6$ is C$_{1-6}$ alkyl, C$_{1-6}$ alkyloxy-C$_{1-6}$ alkyl or aryl.

When describing the compounds methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 6 carbon atoms. Representative alkyl groups include, by way of example, methyl, ethyl, n-propyl, isopropyl, n-butyl, sec-butyl, isobutyl, tert-butyl, n-pentyl, n-hexyl, and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

In a preferred compound of formula I of the present invention, R$_1$ is methoxy.

In an alternative preferred compound of formula I of the present invention, R$_2$ and R$_3$ together form a double bond or an oxo.

In a further preferred compound of formula I of the present invention, R$_2$ is OH and R$_3$ is methyl-OH.

In a further preferred compound of formula I of the present invention, R$_4$ is tert-butyldimethylsilyloxy.

In a more preferred compound of formula I of the present invention, R$_5$ and R$_6$ are phenyl.

The president also provides a compound having formula II wherein X$_1$ is hydrogen, acyl, C$_{1-6}$ alkylsilyl or C$_{1-6}$ alkyloxy-C$_{1-6}$ alkyl;

X$_2$ is hydrogen, acyl, C$_{1-6}$ alkylsilyl or C$_{1-6}$ alkyloxy-C$_{1-6}$ alkyl;

R$_5$ is C$_{1-6}$ alkyl, C$_{1-6}$ alkyloxy-C$_{1-6}$ alkyl or aryl; and R$_6$ is C$_{1-6}$ alkyl, C$_{1-6}$ alkyloxy-C$_{1-6}$ alkyl or aryl.

The president further provides a process for preparing a compound having a formula wherein X$_2$ is hydrogen, acyl, C$_{1-6}$ alkylsilyl or C$_{1-6}$ alkyloxy-C$_{1-6}$ alkyl; and R$_4$ is hydrogen, OH, O-acyl, O—C$_{1-6}$ alkylsilyl or C$_{1-6}$ alkyloxy-C$_{1-6}$ alkyl; said process comprising reacting an intermediate compound of formula 16

16

14 with n-butyl lithium and a compound having a following formula wherein $R_7$ is $C_{1-6}$ alkylsilyloxy, in dry tetrahydrofuran (THF).

In the process of the present invention, the compound of formula 16 is prepared by reacting acid with the compound of formula 15

15 wherein $R_1$ is $C_{1-6}$ alkoxy and $R_4$ is O—$C_{1-6}$ alkylsilyl or $C_{1-6}$ alkyloxy-$C_{1-6}$ alkyl; at 0~65° C.

In the process of the present invention, the compound of formula 15 is prepared by converting the compound of formula 14 wherein $R_1$ is $C_{1-6}$ alkoxy; with TBDMS-chloride in the presence of amine (such as imidazole) in an organic solvent (such as $CH_2Cl_2$) at 0~30° C.

In the process of the present invention, the compound of formula 14 is obtained by reacting a compound of formula 13

13 wherein $R_1$ is $C_{1-6}$ alkoxy; in an organic solvent (such as toluene) and an amine (such as triethylamine), with a sulfonyl chloride (such as MsCl) in dry toluene and $LiAlH_4$ in dry THF at −78~20° C.

In the process of the present invention, the compound of formula 13 is prepared by converting a compound of formula 12 via hydride reduction

12 wherein $R_1$ is $C_{1-6}$ alkoxy.

In the process of the present invention, the compound of formula 12 is prepared by converting a compound of formula 11

11 wherein $R_1$ is $C_{1-6}$ alkoxy; $R_2$ is OH; and $R_3$ is methyl-OH; with $NaIO_4$.

In the process of the present invention, the compound of formula 12 is prepared by converting a compound of formula 10 via ozonolysis

10

$R_1$ is $C_{1-6}$ alkoxy.

In the process of the present invention, the compound of formula 11 is prepared by converting a compound of formula 10

10 with $OsO_4$ in pyridine.

In the process of the present invention, the compound of formula 10 is prepared by converting an intermediate compound of formula 9

9 with acetic anhydride (Ac$_2$O) in the presence of amine (such as pyridine).

In the process of the present invention, an intermediate compound of formula 9 is prepared by converting an intermediate compound of formula 8

8 with SeO$_2$ and t-butylhydroperoxide in CH$_2$Cl$_2$ and pyridine −10~30° C.

In the process of the present invention, an intermediate compound of formula 8 is obtained by reacting (20S)-idomethyl-Cyclovitamin D$_2$ in dry THF with diphenylphosphine, n-butyllithium and H$_2$O$_2$ at −78~30° C.

EXAMPLE

The examples below are non-limited and are merely representative of various aspects and features of the present invention.

Example 1

Preparation of SO$_2$-Adduct of (3S)-tosylate-(20S)-hydroxymethyl-9,10-secoergosta-5,7(E),10(19),22(E)-triene (4)

Into a 2 L G/L, three-neck, round-bottom flask equipped with a mechanical stirrer, was charged vitamin D$_2$ (50 g, 126 mmol), dichloromethane (75 mL), pyridine (75 mL), 4-dimethylaminopyridine (DMAP, 3 g, 24.56 mmol) and p-toluene-solfonyl chloride (36 g, 188.8 mmol) under nitrogen.

The mixture was allowed to react for 24 hr at below 10° C., and was then quench with 50 mL of 10% NaHCO$_3$(aq). The aqueous phase was extracted with ethyl acetate (100 mL×2) and the ether acetate extract was washed with 10% NaHCO$_3$ (100 mL×2), and H$_2$O (100 mL×2). The solvent was removed in vacuo and the crude residue (74.3 g, Vitamin D$_2$ 3-tosylate).

This residue was dissolved in methylene chloride (300 mL) and added H$_2$O (25 mL). The mixture was cooled to below 10° C., and then sulfur dioxide was bubbled into the solution for about 1 hour until the completion of the reaction (monitored by TLC). After reaction completion, the excess SO$_2$ gas was removed under vacuum to obtain a residue. The residue was dissolved in ethyl acetate (EA, 200 mL) and washing by 10% NaHCO$_3$ (200 mL). After phase separated, the organic layer obtained was concentrated to dryness under vacuum to obtain orange foam.

This orange foam was dissolved in methylene chloride (300 mL) and methanol (30 mL), 10% NaHCO$_3$ (30 mL) were added. The mixture is cooled to −10° C. Ozone (generated from Oxygen, using Ozoner generator) was bubbled through the solution for 2 hour until TLC analysis (silica gel plates, 20% ethyl acetate in hexanes) indicated no further change.

The reaction mixture was purged with oxygen for 5 minutes, and sodium borohydride (6 g, 88.23 mmol) was added in five portions over 1 hours. The resulting mixture was stirred for 1 hour at room temperature. At this point, 0.5N aqueous hydrochloric acid solution (100 mL) was slowly added, and the mixture was extracted with 50% ethyl acetate in hexanes (200 mL×3). The combined organic extracts were washed with 10% NaHCO$_3$ (200 mL×3), dried over anhydrous magnesium sulfate, and filtered. The filtrate was evaporated under reduced pressure to obtain 86 g of 4 (a mixture of isomers) as orange foam that used without purification in the next step.

Example 2

Preparation of (20S)-hydroxymethyl-Cyclovitamin (5)

To a 2 L, three-neck, round-bottom flask equipped with a reflux condenser, mechanical stirrer, thermocouple was charged with the SO$_2$-Adduct of (3S)-tosylate-(20S)-hydroxymethyl-9,10-secoergosta-5,7(E),10(19),22(E)-triene (86 g, 156.7 mmol), sodium bicarbonate (100 g, 1.2 mol), and methanol (750 mL). The resulting suspension was heated under reflux for 2.5 hour or until TLC analysis (silica gel plates, 30% ethyl acetate in hexanes) indicated that no starting material remained. The reaction mixture was cooled to room temperature and filtered, and the filtrate was concentrated under reduced pressure. The crude residue was dissolved in ethyl acetate (200 mL) and washed with H$_2$O (200 mL×2). The extracts was dried over anhydrous magnesium sulfate and filtered. The filtrate was evaporated under reduced pressure to obtain 58 g of 5 as yellow foam that was used without purification in the next step.

Silica gel column chromatography (20% ethyl acetate in hexanes as eluant) provided a compound 6 (mixtures, 6R & 6S) as yellow oil:

NMR (CDCl$^3$, 600 Hz): δ4.94~4.99 (2H, m, 19-H), 4.84 (isomer, 1H, s, 19-H), 4.18 (isomer, 1H, s, 19-H), 4.65 (isomer, 1H, d, J=8.76 Hz, 7-H), 4.42 (isomer, 1H, d, J=8.82 Hz, 7-H), 4.16 (m, 1H), 3.60~3.61 (1H, m, 22-H), 3.35~3.41 (1H, m, 22-H), 3.28&3.21 (3H, s, OCH$_3$), 1.02 (3H, d, J=6.6 Hz, 21-CH$_3$), 0.56 (3H, s, 18-CH$_3$).

Example 3

Preparation of (20S)-iodomethyl-Cyclovitamin D$_2$ (7)

In 2 L, three-neck, round-bottom flask equipped with a mechanical stirrer, thermocouple was charged with 5 (58 g, 0.17 mol), dichloromethane (75 mL), pyridine (75 mL), DMAP (3 g, 24.56 mmol) and p-toluene-solfonyl chloride (36 g, 188.8 mmol) under nitrogen.

The mixture is allowed to react for 2 hr at 30° C., and is then quench with 50 mL of 10% NaHCO$_3$(aq). The aqueous phase is extracted with ethyl acetate (100 mL×2) and the ether acetate extract is washed with 10% NaHCO$_3$ (100 mL×2), and H$_2$O (100 mL×2). The solvent is removed in vacuo and the crude residue (75 g, 0.15 mol, (20S)-tosylate-Cyclovitamin D$_2$). The residue was dissolved in acetone (500 mL) and sodium iodine (38 g, 0.25 mol). The mixture was under reflux for 2.5 hour or until TLC analysis (silica gel plates, 20% ethyl acetate in hexanes) indicated that no starting material remained. The reaction mixture was cooled and the solvent was evaporated under reduced pressure to afford a residue. The residue was dissolved in ethyl acetate (200 mL) and washed with H$_2$O (200 mL×3). The extracts was dried over an). The extracts was dried over anhydrous magnesium sulfate and filtered. The filtrate was evaporated under reduced pressure to obtain 40 g (0.088 mol) of Compound 7 as orange foam that was used without purification in the next step.

$^1$HNMR (CDCl$_3$, 200 Hz): δ4.98 (d, 1H, J=10.82 Hz), 4.83 (d, 1H, J=11.62 Hz), 4.67 (d, 1H, J=8.76 Hz), 4.44 (d, 1H, J=8.90 Hz), 3.36 (m, 1H), 3.20 (m, 1H), 3.21&3.29 (s, 3H), 1.01 (d, 3H, J=5.72 Hz), 0.56 (s, 3H).

Example 4

Preparation of (20S)-(diphenylphosphonium)-Cyclovitamin D$_2$ (8)

In 2 L, three-neck, round-bottom flask equipped with a mechanical stirrer, thermocouple, nitrogen bubbler, and two pressure-equalizing addition funnels was charge diphenylphosphine (12.96 g, 69.61 mmol) and dry THF (320 mL). The stirrer was started, and the solution was cooled to −78° C. To one addition funnel was charged n-butyllithium (1.5M solution in hexanes, 50 mL, 75 mmol), and this was slowly added to the cooled solution, producing a reddish-orange mixture that was stirred at −78° C. for 45 minutes. A solution of compound 7 (40 g, 88 mmol) in dry THF (160 mL) was transferred to the second addition funnel, and this solution was added to the reaction stirred for 45 minutes at −78° C. and then gradually warmed to ambient temperature where it was stirred for 3 hour. The reaction mixture was diluted with methyl tert-butyl ether (TBME, 320 mL) and washed with saturated aqueous ammonium chloride solution (150 mL). The organic layer was gently washed with 10% hydrogen peroxide solution (10% H$_2$O$_2$, 320 mL×3). The organic layer was then washed with saturated aqueous sodium chloride solution (150 mL×2), dried over anhydrous magnesium sulfate, and clarified. The yellow filtrate was evaporated under reduced pressure to afford the crude product as yellow oil (32 g). Silica gel column chromatography (30% ethyl acetate in hexanes as eluant) provided a 34% yield of compound 8 (mixtures) as yellow oil:

$^1$HNMR (200 MHz, CDCl$_3$): δ7.67~7.77 (m, 4H), 7.46~7.41 (m, 6H), 4.93 (m, 1H), 4.79 (m, 1H), 4.43 (1H, m), 4.14 (m, 1H), 3.26&3.21 (s, 3H, 6-OCH$_3$, 6R&6S isomer), 1.29~1.23 (m, 2H), 1.08 (s, 3H), 0.48 (s, 3H).

Example 5

Preparation of (20S)-(diphenylphosphonium)-1-hydroxyl-Cyclovitamin D$_2$ (9)

In 2 L, three-neck, round-bottom flask equipped with a mechanical stirrer, thermocouple, nitrogen bubbler was charged with 8 (16.8, 31.77 g mmol), SeO$_2$ (2.0 g, 18.01 mmol), CH$_2$Cl$_2$ (250 mL) and pyridine (3 mL). The mixture was cooled below 15° C., and then tert-butyl hydroperoxide (70% t-BuOOH in water, 17.7 mL) was added. The mixture was allowed to react for 5 hr, and was then quench with 1700 mL of 10% NaHCO$_{3(aq)}$. The aqueous phase was extracted with ethyl acetate (500 mL×2) and the ether acetate extract was washed with 10% NaHCO$_3$ (100 mL×2), and H$_2$O (100 mL×2). The solvent was removed in vacuo and the crude residue {22.4 g, (20S)-(diphenylphosphonium)-1-hydroxyl-Cyclovitamin D$_2$}. Silica gel column chromatography (30% ethyl acetate in hexanes as eluant) provided 5.2 g (30% yield) of compound 9 (mixtures) as yellow oil $^1$HNMR (600 MHz, CDCl$_3$): δ7.68~7.72 (m, 4H), 7.39~7.48 (m, 6H), 5.06~5.24 (m, 2H), 4.88 (d, 1H, J=9.7 Hz), 4.61 (d, 1H, J=8.82 Hz), 4.42~4.32 (m, 1H), 3.26&3.19 (s, 3H, 6-OCH$_3$, 6R & 6S isomer), 1.29~1.23 (m, 2H), 1.08 (d, 3H, J=6.1 Hz), 0.48 (s, 3H).

Example 6

Preparation of 1α-acetoxy-3,5-cyclo-(20S)-(diphenylphosphonium)-10-hydroxyl-cyclovitamin D2 1-acetate, 6-methyl ether (10)

Compound 9 (4 g, 7.34 mmol, R═H)) was dissolved in dry pyridine (20 mL) and acetic anhydride (3.2 ml, 33.85 mmol). The reaction was added 4-Dimethylaminopyridine (DMAP, 0.24 g, 1.96 mmol) and kept at room temperature for about 1 hour, then diluted with 10% NaHCO$_3$ solution (8 mL). This solution is extracted with ethyl acetate (8 mL×3) and the organic extracts were washed with H$_2$O (8 mL×3), dried over MgSO$_4$, and the solvent was removed in vacuo to give crude compound 10 (6.3 g, R═Ac) that was used without purification in the next step.

Example 7

Preparation of 1α-acetoxy-3,5-cyclo-(20S)-(diphenylphosphonium)-10-oxo-19-nor vitamin D2 1-acetate,6-methyl ether (12)

(a). 10,19-dihydro-1α-trihydroxy-3,5-cyclo-(20S)-(diphyenylphosphonium)-vitamin D2 1-acetate,6-methyl ether (11)

Intermediate compound 10 (4.02 g, 6.85 mmol) was treated with slight molar excess of osmium tetroxide in pyridine according to the general procedure described by Paaren et al., "Electrophilic Addition of OsO$_4$ to 25-hydroxhchlolecaliferol and Its 3,5-cclo derivative", J. Org. Chem. 48, 3819, 1983, to obtain the 10,19-dihydroxylated derivative compound 11 (R=Ac). Silica gel column chromatography (20% ethyl acetate in hexanes as eluant) provided 2.22 g (3.57 mmol) of compound 11 as yellow oil.

(b). 1α-acetoxy-3,5-cyclo-(20S)-(diphenylphosphonium)-10-oxo-19-nor vitamin D2 1-acetate,6-methyl ether (12, R=Ac)

The 10,19-dihydroxylated intermediate compound 11 (2.22 g, 3.58 mmol) was treated with a solution of sodium metapariodate according the described by Paaren et al[2]. (J. Org. Chem. 48, 3819, 1983) to obtain produce the 10-oxo-cyclovitamin D derivative (compound 12, R=Ac, 2.51 g).

It has been found also that this diol cleavage reaction does not require elevated temperatures, and it is, indeed, generally preferable to conduct the reaction at approximately room temperature.

Example 8

Preparation of 1α-acetoxy-3,5-cyclo-(20S)-(diphenylphosphonium)-10-oxo-19-nor vitamin D2 1-acetate,6-methyl ether (12, R=Ac)

Compound 10 (0.5 g, 0.85 mmol) was dissolved in methylene chloride (1 mL) and methanol (0.4 mL), 10% NaHCO$_3$ (0.4 mL) were added. The mixture was cooled to −10° C. Ozone (generated from Oxygen, using Ozoner generator) was bubbled through the solution for 1 hour until TLC analysis (silica gel plates, 20% ethyl acetate in hexanes) indicated no further change.

The reaction mixture was purged with oxygen for 5 minutes, and Me$_2$S (0.4 mL) was added. The resulting mixture was stirred for 1 hour at room temperature. The reaction mixture was concentrated to dryness. Silica gel column chromatography (20% ethyl acetate in hexanes as eluant) provided a 0.2 g of compound 12 as yellow oil.

Example 9

Preparation of 1α-acetoxy-3,5-cyclo-(20S)-(diphenylphosphonium)-10-hydroxyl-19-nor vitamin D2 1-acetate,6-methyl ether 1-acetate (13)

In 100 mL, three-neck, was charged the 10-oxo derivative compound 12) (R=Ac, 2.51 g, 4.04 mmol), methanol (6.66 mL) and THF (13.32 mL) and cerium (III) chloride hexahydrate (3.0 g, 8.08 mmol). The mixture was agitated and cooled to below 10° C. followed by the addition of sodium borohydride (0.15 g, 4.04 mol). After reaction completion, the reaction mixture was quenched by the addition of saturated ammonia chloride solution (10 mL), the mixture was agitated for about 30 minutes and then concentrated under vacuum to give residue. To the residue was added 50% ethyl acetate in hexanes (10 mL×3) followed by phase separation. The organic extracts was washed with aqueous NaHCO$_3$ (10 mL), followed by phase separation. The organic layer was washed with water (10 mL×2), followed by concentrated to dryness under vacuum to give compound 13 crude (1.89 g).

$^1$HNMR (200 MHz, CDCl$_3$): δ7.70~7.78 (m, 4H), 7.42~7.49 (m, 6H), 4.65~4.50 (m, 2H), 4.21~4.18 (m, 1H), 3.94 (br, 1H), 3.41 (major isomer, s, 3H, 6-OCH$_3$), 3.18 (minor isomer, s, 3H, 6-OCH$_3$), 2.25~2.53 (m, 1H), 2.36~2.40 (m, 1H), 2.03 (s, 3H, OAc), 1.05 (3H, m, 21-CH$_3$), 0.45 (3H, s, 18-CH$_3$).

Example 10

Preparation of 1α-(tert-Butylmethylsilyloxy)-3,5-cyclo-(20S)-(diphenylphosphonium)-19-nor vitamin D2 1-(tert-Butylmethylsilyloxy),6-methyl ether 1-(tert-Butylmethylsilyloxy) (15)

The 10-alcohol (R=Ac, compound 13, 1.89 g, 3.20 mmol) was dissolved in anhydrous Toluene and triethylamine (1.91 g, 18.9 mmol). The mixture was cooling to below 0° C., followed by added mesyl chloride solution (0.52 g, 4.52 mmol, 0.35 mL mesyl chloride in 3.5 mL anhydrous Toluene). The mixture was stirred at 0° C. for 2 hour or until the reaction completed. The LiAlH$_4$ (0.72 g, 18.97 mmol) was added, and followed by anhydrous THF (5 mL) added at 0° C. The mixture kept at 0° C. for 2 h. Excess LiAlH$_4$ was decomposed with H$_2$O, followed by phase separation. The organic layer was washed by water and dried over MgSO$_4$, filtered and evaporated to give the crude 19-nor product (compound 14). The compound 14 crude is purified by fraction collection using the flash column chromatography to give compound 14(0.69 g, 1.29 mmol).

The compound 14(0.69 g, 1.29 mmol) was dissolved in dichloromethane (4.2 mL), and imidazole (0.26 g, 3.88 mmol) and TBDMS-chloride (0.29 g, 1.92 mmol) were added. The mixture was stirred at 20° C. for 90 minutes and then partitioned between EtOAc (10 mL) and water (10 mL). The organic layer was washed twice with water and brine, dried and concentrated to give a crude product (Compound 15, 0.80 g).

$^1$HNMR (600 MHz, CDCl$_3$): δ7.70~7.74 (m, 4H), 7.41~7.49 (m, 6H), 4.91 (d, 1H, J=9.18 Hz), 4.08~4.09 (minor isomer, m, 1H, 7-H), 3.90~3.87 (major isomer, m, 1H, 7-H), 3.76 (d, 1H, J=9.18 Hz), 3.18 (major isomer, s, 3H, 6-OCH$_3$), 3.13 (minor isomer, s, 3H, 6-OCH$_3$), 2.25~2.53 (m, 1H), 2.36~2.40 (m, 1H), 1.05 (3H, m, 21-CH$_3$), 0.84 (s, 9H), 0.45 (3H, s, 18-CH$_3$), 0.05 (s, 6H).

Example 11

Preparation of 1α-acetoxy-3-(tert-Butyldimethylsilyloxy)-(20S)-(diphenylphosphonium)-19-nor vitamin D$_2$ (16)

The compound 15 (5.11 g, 7.9 mmol) was dissolved in acetic acid (51 mL) and stirred at 55° C. for 1 hour. The mixture was cooled, ice water added extracted with ethyl acetate. The other phase was washed with cold 10% sodium bicarbonate solution, brine, dried over with MgSO$_4$, filtered and evaporated to give the crude compound 16 (6.19 g). The crude compound 16 was purified by column chromatography to give compound 16.

$^1$HNMR (200 MHz, CDCl$_3$): δ7.67~7.76 (m, 4H), 7.46~7.44 (m, 6H), 6.17 (d, 1H, J=11.12 Hz), 5.78 (d, 1H, J=Hz), 5.06 (br, 1H), 3.96 (br, 1H), 2.46 (m, 3H, 3-COCH$_3$), 1.03~1.06 (m, 2H, 22-CH$_2$), 0.83~0.86 (m, 12H), 0.42 (s, 3H), 0.02 (s, 6H).

Example 12

Intermediate for Side Chain (A) Preparation of Diol (Compound S1)

50 g (0.42 mol) of methyl(S)-(−)-3-hydroxy-2-methylpropionate was dissolved in 250 mL of anhydrous tetrahydrofuran and added under nitrogen atmosphere and ice cooling to a stirred solution of 720 mL (2.18 mol) of methylmagnesium Chloride (22% in THF) solution in ether. At the end of the addition 100 mL of anhydrous tetrahydrofuran was added to facilitate stirring. The mixture was stirred at room temperature for 2 hrs, decomposed by the careful addition of 150 mL of 5N HCl with ice cooling and extracted three times with 200 mL of ether. Each extract was washed with 150 mL of saturated NaCl solution, combined and dried over $Na_2SO_4$. Evaporation afforded 52.3 g of crude diol as yellow oil. The crude diol is purified by fraction collection using the flash column chromatography to give diol (compound S1, 47 g, 0.40 mol).

$^1$HNMR (200 MHz, $CDCl_3$): δ3.62~3.74 (m, 2H), 3.00 (s, 2H, OH), 1.73~1.84 (m, 1H), 1.28 (s, 3H, $CH_3$), 1.18 (s, 3H, $CH_3$), 0.82 (d, J=7.08 Hz, $CH_3$).

(B). Preparation of Aldehyde (Compound S2)

47 g (0.40 mol) of diol was dissolved in 94 mL of Toluene and water (7 mL). To this solution was added NaBr (12.3 g, 0.12 mol), TEMPO (6.24 g, 0.04 mol). The mixture was stir about 30 minutes. Then, to the mixture was added 12% NaOCl (620 mL, 1.0 mol).

The mixture was stirred for 90 minutes and then phase separation and extracted by Toluene (560 mL×3). The organic layer was washed twice with water and brine, dried and concentrated to give a crude product (compound S2, 46.03 g).

The crude diol was purified by fraction collection using the flash column chromatography (30% ethyl acetate in hexanes as eluant) to give compound S2 (14 g, 0.12 mol).

(C). Preparation of Compound S3

In 100 mL, three-neck, was charged the compound S2 (14 g, 0.12 mol), imidazole (0.82 g, 12.0 mol) and TEA (98.1 g, 0.97 mol). The mixture was agitated and cooled to below 10° C. followed by the addition of trimethylsily chloride (TMS-Cl, 72.3 g, 0.66 mol). After reaction completion, the reaction mixture was quenched by the addition of water (125 mL), the mixture was agitated for about 30 minutes and then phase separation, the organic layer was concentrated under vacuum to give residue (24.24 g). The compound S3 crude was purified by fraction collection using the flash column chromatography (10% ethyl acetate in hexanes as eluant) to give compound S3 (10.4 g, 55.2 mmol).

$^1$HNMR (200 MHz, $CDCl_3$): δ9.80 (s, 1H), 2.01~2.37 (m, 1H), 1.29 (s, 3H, $CH_3$), 1.21 (s, 3H, $CH_3$), 1.01 (d, J=7.0 Hz, CH3), 0.08 (s, 9H, TMS)

Example 13

Preparation of Compound 17

To a 200 mL, three-neck, round-bottom, flask equipped with a mechanical stirrer, thermocouple, addition funnel, and nitrogen bubbler was charged a solution of compound 16 (4.98 g, 7.9 mmol) in dry THF (49.8 mL). The solution was cooled to −78° C., and n-butyllithium (1.33M solution in hexanes, 6.53 mL, mmol) was added, producing a red solution that was stirred for 45 minutes. At this point, a solution of compound S3 (1.63 g, 8.65 mmol) in dry THF (10 mL) was added over 20 minutes. This solution was stirred at −78° C. for 1 hour, producing a yellow solution. The solution was warmed to 0° C. over 1.5 hour at which ethyl acetate (50 mL) was added. The reaction solution was washed with saturated aqueous ammonium chloride solution (50 mL), water (50 mL), and saturated aqueous sodium chloride solution (50 mL). The organic layer was dried over anhydrous $MgSO_4$ and clarified, and the solvents were evaporated under reduced pressure to afford yellow oil (8.33 g). This oil was dissolved in dry THF (68 mL) and transferred to a dry, 200 mL, three-neck, round-bottom flask equipped with a mechanical stirrer, thermocouple, nitrogen bubbler, and a rubber septum. The reaction was cooled to −12° C., and solid potassium t-butoxide (4.25 g, 37.8 mmol) was added, producing an orange reaction mixture. The reaction mixture was allowed to stir at this temperature for 3 hour at which point it was diluted with ethyl acetate (50 mL) and washed water (20 mL×2), and saturated aqueous sodium chloride solution (20 mL×2). The organic extracts were dried over anhydrous $MgSO_4$ and clarified, and the solvent was evaporated under reduced pressure, affording 6.34 g of crude compound 17 as oil. This oil was purified by column chromatography to afford Compound 17 (1.44 g, 2.51 mmol).

$^1$HNMR (200 MHz, $CDCl_3$): δ6.18 (d, 1H, J=11.6 Hz, 6-H), 5.80 (d, 1H, J=11.6 Hz, 7-H), 5.45~5.29 (m, 2H, 22&23-H), 5.08 (br, 1H, 1-H), 3.96 (br, 1H, 3-H), 2.42 (s, 3H, 3-$COCH_3$), 1.12 (d, 6H, J=7.6 Hz), 0.95 (s, 3H, 1-$CH_3$), 0.86~0.83 (m, 9H), 0.52 (s, 3H, 18-$CH_3$), 0.03 (s, 6H).

Example 14

Preparation of Paricalcitol

The compound 17 (1.44 g, 2.51 mmol) was dissolved in a methanol (14.4 mL), $CH_2Cl_2$ (10 mL) and 20% NaOH (4.5 mL) was added. The mixture was stirred under nitrogen atmosphere for 2 hour. After reaction completion, the reaction mixture was concentrate to remove organic solvent. The residue was extract by ethyl acetate (14.4 mL). The organic phase washed with brine, dried over $MgSO_4$, filtered and evaporated to give residue (1.5 g) that used without purification in the next step.

The residue obtained by above was dissolved in THF (14.4 mL), and Imidazole (0.03 g, 0.44 mmol), TBAF (tertabutyamoniafluoride, 1.2 g, 3.80 mmol) were added. The reaction mixture was heated under reflux 1 hour or until TLC analysis (silica gel plates, 50% ethyl acetate in hexanes) indicated that no starting material remained. The reaction was cooled to room temperature, and was concentrated under reduced pressure. The crude residue was dissolved in ethyl acetate (14.4 mL) and washed with $H_2O$ (14.4 mL×2). The extracts was dried over anhydrous magnesium sulfate and filtered. The filtrate was added phenyl boronic acid (0.12 g, 0.98 mmol). The reaction is processed for 1 hours. After the reaction is complete, the reaction mixture is concentrated and purified through a chromatographic column to give compound 1 (Paricalcitol-crude, 260 mg, $R_1$=R=H) and cyclic-1,3-boronate ester of 1.

Paricalcitol NMR:

$^1$HNMR (600 MHz, $CDCl_3$): δ6.29 (d, 1H, J=11.28 Hz), 5.82 (d, 1H, J=11.28 Hz), 5.34~5.28 (m, 2H), 4.10 (br, 1H), 4.02 (br, 1H), 2.76~2.79 (m, 1H), 2.72 (d, J=12.12 Hz, 1H), 2.45 (d, J=13.26 Hz, 1H), 2.17~2.21 (m, 2H), 1.92~2.11 (m, 5H), 1.22~1.79 (M, 13H), 1.15 (s, 3H), 1.11 (s, 3H), 1.01 (d, J=6.6 Hz, 3H), 0.98 (d, J=6.84 Hz, 3H), 0.53 (s, 3H).

$^{13}$CNMR (600 MHz, $CDCl_3$): 143.2, 139.4, 131.3, 129.2, 124.0, 115.4, 72.6, 67.6, 67.4, 56.5, 56.3, 48.3, 45.9, 44.7, 42.3, 40.7, 40.4, 37.3, 29.1, 28.0, 27.2, 26.4, 23.6, 22.4, 21.2, 15.9, 12.5.

Example 15

Crystallization of Paricalcitol from MeOH—CH₂Cl₂-Methyl Formate

Paricalcitol crude (260 mg, Purity: 97.5%) were dissolved in a mixture of 0.5 mL MeOH, 0.05 mL CH₂Cl₂ and 2.6 mL methyl formate with stirring at 25° C. over a period of 30 minutes. The solution was cooled to 0° C., and that temperature was maintained for 1 hour. The crystals were filtered and washed with cold (−10° C.) MeOH—CH₂Cl₂-Methyl formate mixture, then dried at high vacuum in an oven at 25° C. for 16 hour to obtain a yield of 50 mg (Purity: 99.8%)

Crystallization of Paricalcitol from Acetone+CH₂Cl₂

Paricalcitol crude (160 mg, Purity: 97.5%) were dissolved in a mixture of 3.2 mL Acetone, 0.01 mL CH₂Cl₂ with stirring at 25° C. over a period of 30 minutes. The solution was cooled to 0° C., and that temperature was maintained for 1 hour. The crystals were filtered and washed with cold (−10° C.) Acetone-CH₂Cl₂ mixture, then dried at high vacuum in an oven at 25° C. for 16 hours to obtain a yield of 20 mg. (Purity: 99.8%).

What is claimed is:

1. A process for preparing a compound having a formula wherein $X_2$ is hydrogen, acyl, $C_{1-6}$ alkylsilyl or $C_{1-6}$ alkyloxy-$C_{1-6}$ alkyl; and $R_4$ is hydrogen, OH, O-acyl, O—$C_{1-6}$ alkylsilyl or $C_{1-6}$ alkyloxy-$C_{1-6}$ alkyl; said process comprising reacting an intermediate compound of formula 16 with n-butyl lithium and a compound having a following formula wherein $R_7$ is $C_{1-6}$ alkylsilyloxy, in dry THF.

2. The process according to claim 1, wherein the compound of formula 16 is prepared by reacting acid with the compound of formula 15 wherein $R_1$ is $C_{1-6}$ alkoxy and $R_4$ is O—$C_{1-6}$ alkylsilyl or $C_{1-6}$ alkyloxy-$C_{1-6}$ alkyl; at 0~65° C.

3. The process according to claim 2, wherein the compound of formula 15 is prepared by converting the compound of formula 14 wherein $R_1$ is $C_{1-6}$ alkoxy;
with TBDMS-chloride in the presence of an amine in an organic solvent at 0~30° C.

4. The process according to claim 3, wherein the amine is imidazole and the organic solvent is CH₂Cl₂.

5. The process according to claim 4, wherein the compound of formula 14 is obtained by reacting a compound of formula 13

13 wherein R₁ is $C_{1-6}$ alkoxy;

in an organic solvent and an amine, with a sulfonyl chloride, followed by the addition of LiAlH₄ in dry THF at −78~20° C.

6. The process according to claim 5, wherein the organic solvent is toluene; the amine is triethylamine; and sulfonyl chloride is MsCl.

7. The process according to claim 5, wherein the compound of formula 13 is prepared by converting a compound of formula 12 via hydride reduction

12 wherein R₁ is $C_{1-6}$ alkoxy.

8. The process according to claim 7, wherein the compound of formula 12 is prepared by converting a compound of formula 11

11 wherein R₁ is $C_{1-6}$ alkoxy; R₂ is OH; and R₃ is methyl-OH; with NaIO₄.

9. The process according to claim 7, wherein the compound of formula 12 is prepared by converting a compound of formula 10 via ozonolysis

10 wherein R₁ is $C_{1-6}$ alkoxy.

10. The process according to claim 8, wherein the compound of formula 11 is prepared by converting a compound of formula 10

23 wherein R₁ is C₁₋₆ alkoxy;
with OSO₄ in pyridine.

11. The process according to claim 10, wherein the compound of formula 10 is prepared by converting an intermediate compound of formula 9

9

24 wherein R₁ is C₁₋₆ alkoxy;
with acetic anhydride (Ac₂O) in the presence of amine.

12. The process according to claim 11, wherein the amine is pyridine.

13. The process according to claim 11, wherein an intermediate compound of formula 9 is prepared by converting an intermediate compound of formula 8

8 wherein R₁ is C₁₋₆ alkoxy;
with SeO₂ and t-butylhydroperoxide in CH₂Cl₂ and pyridine at −10~30° C.

14. The process according to claim 13, wherein an intermediate compound of formula 8 is obtained by reacting (20S)-iodomethyl-Cyclovitamin D₂ in dry THF with diphenylphosphine and n-butyllithium, followed by the treatment with H₂O₂ at −78~30° C.

* * * * *